United States Patent [19]

Quinlan

[11] 4,164,574

[45] Aug. 14, 1979

[54] USE OF POLYQUATERNARY AMMONIUM METHYLENE PHOSPHONATES AS MICROBIOCIDES

[75] Inventor: Patrick M. Quinlan, Webster Groves, Mo.

[73] Assignee: Petrolite Corporation, St. Louis, Mo.

[21] Appl. No.: 842,147

[22] Filed: Oct. 14, 1977

Related U.S. Application Data

[62] Division of Ser. No. 414,946, Nov. 12, 1973, Pat. No. 4,084,950, which is a division of Ser. No. 237,883, Mar. 24, 1972, Pat. No. 3,792,084.

[51] Int. Cl.$^2$ .............................................. A01N 9/36
[52] U.S. Cl. ................................... 424/199; 424/204; 71/67; 252/180
[58] Field of Search ................. 424/199, 204; 252/180

[56] References Cited

U.S. PATENT DOCUMENTS

| | | | |
|---|---|---|---|
| 2,774,786 | 12/1956 | Erickson | 260/502.5 |
| 2,841,611 | 7/1958 | Bersworth | 260/502.5 |
| 3,738,937 | 6/1973 | Kautsky | 260/502.5 |

OTHER PUBLICATIONS

Chemical Abstracts, vol. 46 (1952), pp. 7996g–7997c.

*Primary Examiner*—V. D. Turner
*Attorney, Agent, or Firm*—Sidney B. Ring; Hyman F. Glass

[57] ABSTRACT

Polyquaternary ammonium methylene phosphonates and uses thereof, particularly as scale inhibitors, chelating agents, bactericides, etc.

10 Claims, No Drawings

USE OF POLYQUATERNARY AMMONIUM METHYLENE PHOSPHONATES AS MICROBIOCIDES

This Application is a division of Ser. No. 414,946, filed Nov. 12, 1973, now U.S. Pat. No. 4,084,950, issued Apr. 18, 1978, which in turn is a division of Ser. No. 237,883, filed Mar. 24, 1972, now U.S. Pat. No. 3,792,084, issued Feb. 12, 1974.

Most commercial water contains alkaline earth metal cations, such as calcium, barium, magnesium, etc., and anions such as bicarbonate, carbonate, sulfate, oxalate, phosphate, silicate, fluoride, etc. When combinations of these anions and cations are present in concentrations which exceed the solubility of their reaction products, precipitates form until their product solubility concentrations are no longer exceeded. For example, when the concentrations of calcium ion and carbonate ion exceed the solubility of the calcium carbonate reaction product, a solid phase of calcium carbonate will form as a precipitate.

Solubility product concentrations are exceeded for various reasons, such as evaporation of the water phase, change in pH, pressure or temperature, and the introduction of additional ions which can form insoluble compounds with the ions already present in the solution.

As these reaction products precipitate on the surfaces of the water-carrying system, they form scale. The scale prevents effective heat transfer, interferes with fluid flow, facilitates corrosive processes, and harbors bacteria. Scale is an expensive problem in many industrial water systems, causing delays and shutdowns for cleaning and removal.

Scale-forming compounds can be prevented from precipitating by inactivating their cations with chelating of sequestering agents, so that the solubility of their reaction products is not exceeded. Generally, this approach requires many times as much chelating or sequestering agent as cation present, and the use of large amounts of treating agent is seldom desirable or economical.

It is known that certain inorganic polyphosphates would prevent such precipitation when added in amounts far less than the concentrations needed for sequestering or chelating. See, for example, Hatch and Rice, "Industrial Engineering Chemistry," Vol. 31, p. 51, at 53; Reiteimeier and Buchrer, "Journal of Physical Chemistry," Vol. 44, No. 5, p. 535 at 536 (May 1940); Fink and Richardson U.S. Pat. No. 2,358,222; and Hatch U.S. Pat. No. 2,539,305. When a precipitation inhibitor is present in a potentially scale-forming system at a markedly lower concentration than that required for sequestering the scale forming cation, it is said to be present in "threshold" amounts. Generally, sequestering takes place at a weight ratio of threshold active compound to scale-forming cation component of greater than about ten to one, and threshold inhibition generally takes place at a weight ratio of threshold active compound to scale-forming cation component of less than about 0.5 to 1.

The "threshold" concentration range can be demonstrated in the following manner. When a typical scale-forming solution containing the cation of a relatively insoluble compound is added to a solution containing the anion of the relatively insoluble compound and a very small amount of a threshold active inhibitor, the relatively insoluble compound will not precipitate even when its normal equilibrium concentration has been exceeded. If more of the threshold active compound is added, a concentration is reached where turbidity or a precipitate of uncertain composition results. As still more of the threshold active compound is added, the solution again becomes clear. This is due to the fact that threshold active compounds in high concentrations also act as sequestering agents, although sequestering agents are not necessarily "threshold" compounds. Thus, there is an intermediate zone between the high concentrations at which threshold active compounds sequester the cations of relatively insoluble compounds and the low concentrations at which they act as threshold inhibitors. Therefore, one could also define "threshold" concentrations as all concentrations of threshold active compounds below that concentration at which this turbid zone or precipitate is formed. Generally the threshold active compound will be used in a weight ratio of the compound to the cation component of the scale-forming salts which does not exceed about 1.

The polyphosphates are generally effective threshold inhibitors for many scale-forming compounds at temperatures below 100° F. But after prolonged periods at higher temperatures, they lose some of their effectiveness. Moreover, in an acid solution, they revert to ineffective or less effective compounds.

I have now discovered a process for inhibiting scale such as calcium, barium and magnesium carbonate, sulfate, silicate, etc., scale which comprises employing threshold amounts of polyquaternary ammonium methylene phosphonates.

The term "polyquaternary ammonium methylene phosphonates" includes compositions containing at least two quaternary ammonium groups therein, and having at least one methylene phosphonate group attached to at least one of the nitrogens of the quaternary ammonium groups, but preferably having at least 4 methylene phosphonate groups in the composition.

The compositions of this invention are polyquaternary ammonium methylene phosphonates. Stated another way, the compositions of this invention have a plurality of nitrogen atoms which have been converted to the quaternary state by having (1) nitrogen-bonded methylene phosphonates
(2) nitrogen-bonded hydrocarbon groups such as alkyl, alkenyl, aryl, aralkyl, alkaryl, etc.

The quaternary nitrogen are joined together by any suitable bridging means, such as for example a hydrocarbon group such as alkylene, alkenylene, aryl group such as alkaralkylene such as

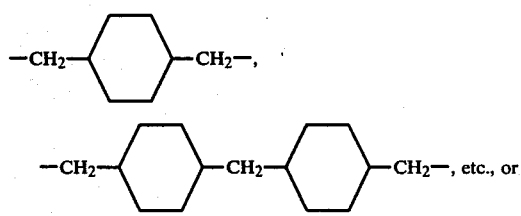

hydrocarbon group containing other than carbon and hydrogen, for example alkyletheralkylene such as

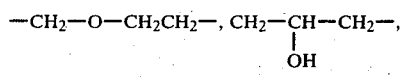

etc.

Although the polymer may be prepared from unsubstituted mono- or polyamines, followed by substitution in the nitrogen groups, in order to better control the desired products the amines are substituted prior to polymerization. For example, rather than reacting as follows:

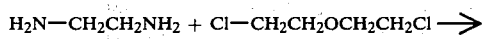

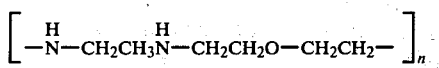

and then which is phosphonethylolated to yield

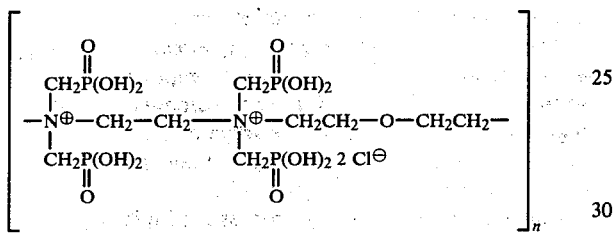

The following reaction can be carried out, where the polyamine in first phosphomethylated:

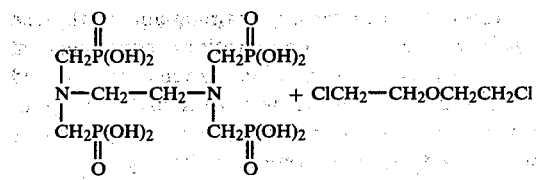

to yield the same product.

In addition, the polymeric quaternaries may be formed by reacting:

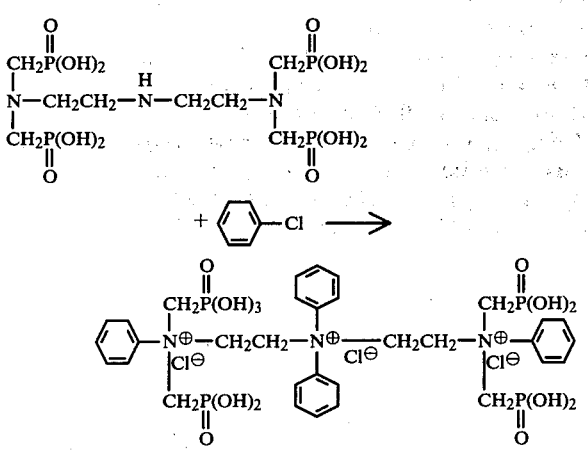

Stated another way, the amine is first phosphomethylolated to the desired degree, and this product is then quaternized with a suitable quaternization agent. The monohalide is employed if one does not desire to extend the number of amino groups or by a polyhalide if one desires to extend the number of amino groups.

The amines employed herein are phosphomethylolated preferably by the Mannich reaction as illustrated in the following reaction where —NH indicates at least one reactive group on the polyamine:

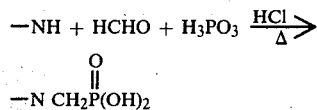

The Mannich reaction is quite exothermic and initial cooling will generally be required. Once the reaction is well under way, heat may be required to maintain refluxing conditions. While the reaction will proceed at temperatures over a wide range, i.e., from 80° to 150° C., it is preferred that the temperatures of the reaction medium be maintained at the refluxing temperatures. The reaction is preferably conducted at atmospheric pressure, although sub-atmospheric and superatmospheric pressures may be utilized if desired. Reaction times will vary, depending upon a number of variables, but the preferred reaction time is 1 to 5 hours, and the most preferred reaction time is 2½ to 3½ hours.

Although the phosphonic acid or the formaldehyde may be added in either order, or together to the reaction mixture, it is preferred to add the phosphonic acid to the amine and then to slowly add the formaldehyde under refluxing conditions. Generally, about ½ to 10 moles or more of formaldehyde and about ½ to 10 moles or more of phosphonic acid can be used per mole equivalent of amine, although the most preferred molar equivalent ratios of formaldehyde:phosphonic acid:amine is 1:1:1. Excess formaldehyde and/or phosphonic acid function essentially as solvents, and thus there is no real upper limit on the amount of these materials which may be used, per mole equivalent of amine, although such excess amounts naturally add to the cost of the final product and are therefore not preferred. The preferred molar equivalent ratios are ½ to 2 moles each of the formaldehyde and phosphonic acid per mole equivalent of amine.

The Mannich reaction will proceed in the presence or the absence of solvents. The reaction may be carried out as a liquid-phase reaction in the absence of solvents or diluents, but is preferred that the reaction be carried out in an aqueous solution containing from about 40 to about 50% of the reaction monomers. Preferred conditions for the Mannich reaction include the use of formaldehyde based on the molar equivalent amount of the amine compound, the use of a stoichiometric amount of phosphonic acid based on the molar equivalent amount of amine (e.g., on the amine active hydrogen content), refluxing conditions and a pH of less than 2 and preferably less than 1.

Although formaldehyde is preferred, other aldehydes or ketones may be employed in place of formaldehyde such as those of the formula

where R and R' are hydrogen, or a hydrocarbon group such as alkyl, i.e., methyl, ethyl, propyl, butyl, etc., aryl, i.e., phenyl, alkylphenyl, phenalkyl, etc., cycloalkyl, i.e., cyclohexyl, etc.

The compound can also be prepared by a modified Mannich reaction by employing a chloromethylene phosphonate.

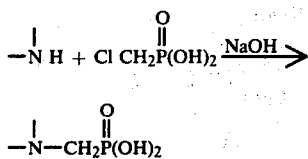

X-Z-X may be a wide variety of polymerizing compounds, i.e., capable of joining amino groups, where Z may be alkylene, alkenylene, alkynylene, alkaralkylene, an alkyleneether-containing group, an ester-containing group, an amido-containing group, etc., and X is a halide.

The following are non-limiting examples:

I. Saturated dihalides

where Z is alkylene, straight chain or branched, for example $X(CH_2)_nX$ where n is 2-25 or more, for example 2-10, but preferably 2-4. The $-(CH_2)_n-$ may be branched such as where at least one of the H's is a hydrocarbon group such as alkyl, i.e., methyl, ethyl, etc., substituted such as halo, hydroxy, etc.

II. Alkaralkylene dihalides

where Z is aralkylene having for example 8-30 or more carbons, such as 8-20 carbons, but preferably xylylene.

The following are illustrative examples:

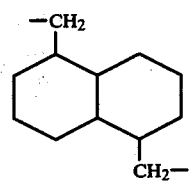

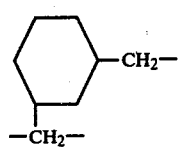

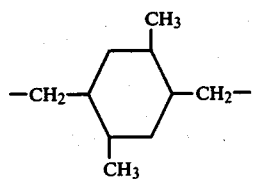

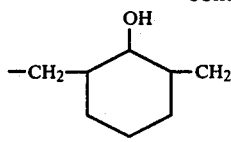

Additional examples of alkaralkylene radicals include those of the formula $-CH_2-Ar-CH_2-$ where Ar is

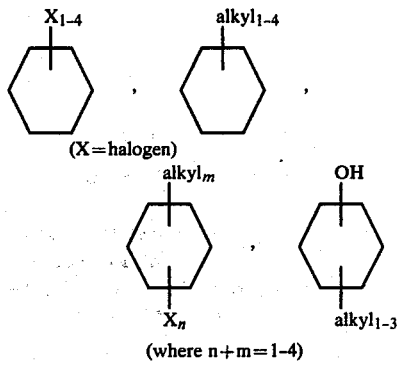

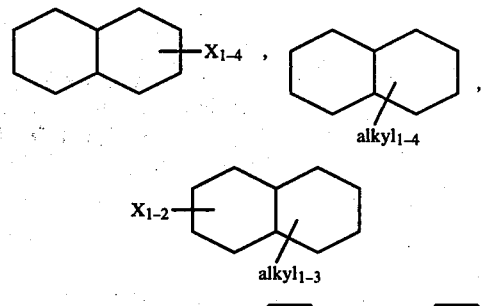

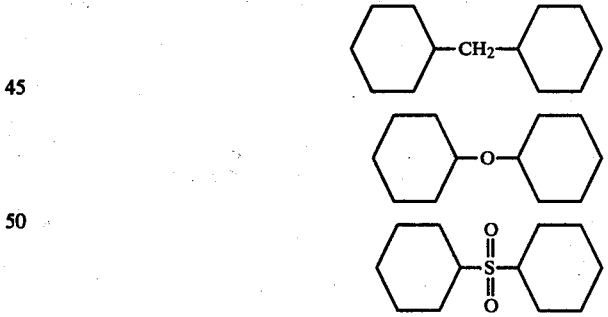

III. Alkylene Ethers

where A is an alkyleneether radical $-A(OA)_{\bar{n}}$ where A is alkylene (including cycloalkylene ether radicals) having for example from 1-10 or more carbons such as 1-4, but preferably 2 in each alkylene unit. Typical examples are

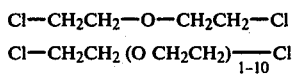

-continued

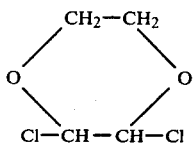

Additional examples of A include groups of the formula $(AO)_n$ where A is

where Y is alkyl, for example

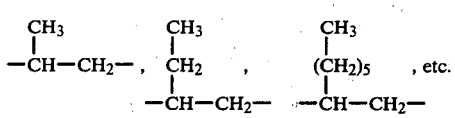

Thus, A can be methylene, polymethylene, ethylene, propylene, butylene, octylene, etc. In addition $(AO)_n$ may be homo or hetero as to A, to yield for example $(ETO)_a(PrO)_b$, $(PrO)_a(BuO)_b$, or $(PrO\text{---}ETO)_n$;

etc.

These compounds also include the formal of ethylene chlorohydrin and bromohydrin, for example $ClCH_2CH_2OCH_2OCH_2CH_2Cl$, $ClCH_2CH_2OCH_2CH_2OCH_2OCH_2CH_2OCH_2CH_2Cl$ etc.

IV. Unsaturated dihalides $$X\text{---}Z\text{---}X$$

where Z is an unsaturated aliphatic radical, for example

$-CH_2-C\equiv C-CH_2-$, etc.

Among the polyamines employed herein are polyalkylenepolyamines, for example, of the formula

where n is an integer, for example 1 to 25 or more, such as 2 to 10, but preferably 2 to 5, etc., and A is an alkylene group $-(CH_2)_m-$ where m is 2 to 10 or more, but preferably ethylene or propylene.

One or more of the hydrogens on the $CH_2$ group may be substituted, for example, by such groups as alkyl groups, for example, methyl, ethyl, etc. Examples of A include

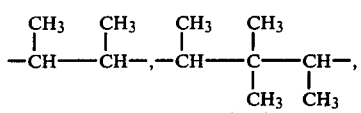

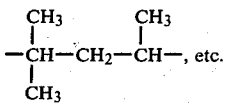

Examples of polyamines include the following: diethylene triamine, dipropylene triamine, triethylene tetramine, tripropylene tetramine, tetraethylene pentamine, tetrapropylene pentamine, polyalkyleneimines, i.e., the higher molecular weight amines derived from alkyleneimine such as polyethyleneimines, polypropyleneimines, for example, having 50, 100 or more alkylene amino units, etc. Mixtures of the above polyamine amines and those polyamines containing both ethylene and propylene groups, for example:

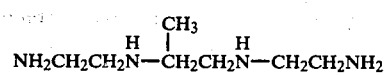

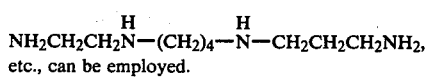

etc., can be employed.

These include the following:

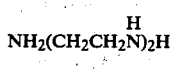

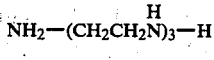

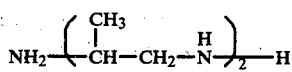

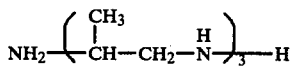

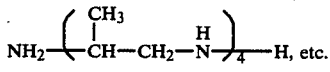

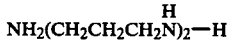

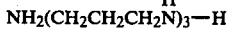

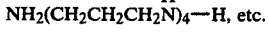

In addition, the starting polyamine may be of a technical grade such as "Amine E-100" from Dow Chemical Company. Amine E-100 is the still bottoms from a polyalkylene polyamine process with the following approximate composition:

| | Percent |
|---|---|
| Tetraethylene pentamine ($H_2N(CH_2CH_2\overset{H}{N})_4H$) | 10 |
| Pentaethylene hexamine ($H_2N(CH_2CH_2\overset{H}{N})_5H$) | 40 |
| Cyclics (piperazines) | 20 |
| Branched structure | 20 |
| Polymers (chains with more than five ethylene | 10 |

Other suitable amines are the polyethyleneimine series from Dow Chemical Company.

Also included within the terms polyalkylene polyamine are substituted polyamines such as N-alkyl, N-aryl, etc., compositions

provided some groups are present capable of forming methylene phosphonates.

Illustrative examples are

where R is alkyl, aryl, alkenyl, etc., such as hexyl, dodecyl, etc.

Also included are acylated polyalkylenepolyamines such as alkyl, aryl, alkenyl, etc., for example, where

is a acetyl, benzoic, etc.

The following equation illustrates the reaction of epichlorohydrin with polyethylenepolyamines, ideally presented:

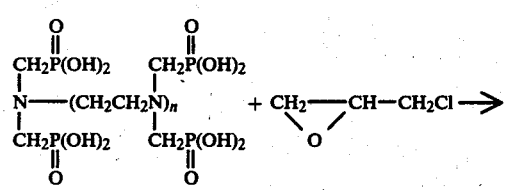

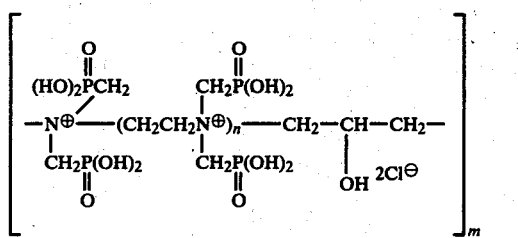

The above is an idealized presentation, but the invention does not exclude other related reactions such as certain amounts of crosslinking, etc.

The reaction with dichlorodiethyl ether may be ideally presented as follows where the R's are

groups:

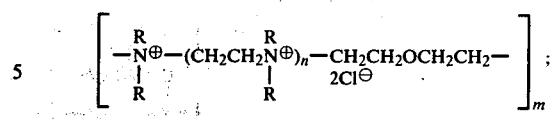

with alkylene dichlorides the reaction is

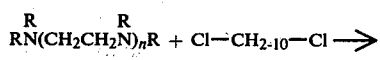

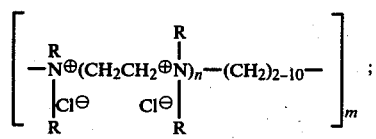

with butene dichloride the reaction is

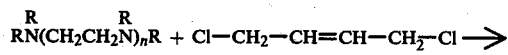

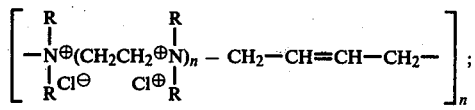

with butyne dichloride the reaction is

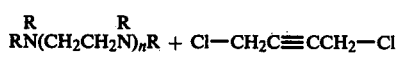

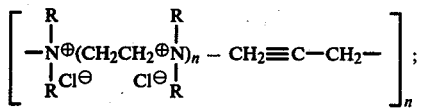

with aralylarylene the reaction is

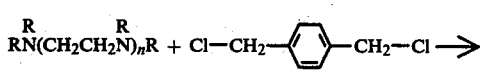

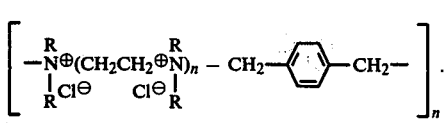

Polyquaternaries can also be prepared from methylene phosphonates of ammonia or monoamines, for example

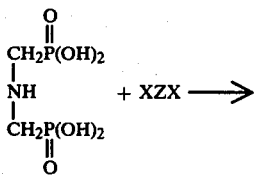

Formula I

-continued

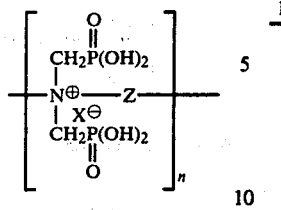

where XZX has the meaning stated above, or according to the equation

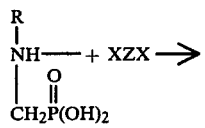 + XZX → Formula II

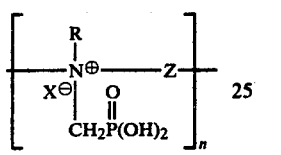

where R is a substituted group such as alkyl, aryl, alkenyl, alkaryl, aralkyl, cycloalkyl, etc.

The following are representative examples.

TABLE I

| Ex. | Formula |
|---|---|
| 1. | 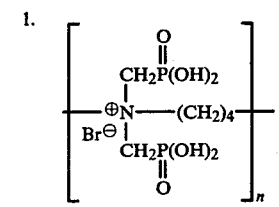 |
| 2. | 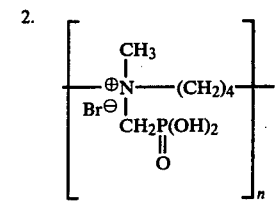 |
| 3. | 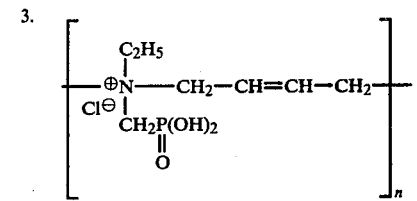 |
| 4. | 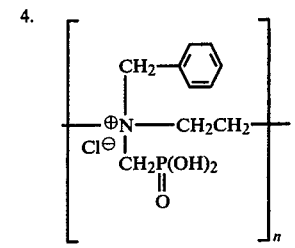 |

TABLE I-continued

| Ex. | Formula |
|---|---|
| 5. | ![formula] —⊕N(CH3)(CH2P(OH)2=O)—CH2CH2OCH2CH2— Cl⊖ |
| 6. | —⊕N(C6H5)(CH2P(OH)2=O)—(CH2)4— Br⊖ |
| 7. | —⊕N(CH3)(CH2P(OH)2=O)—CH2—C6H4—CH2— Cl⊖ |
| 8. | —⊕N(CH2P(OH)2=O)2—CH2—CH=CH—CH2— Cl⊖ |
| 9. | —⊕N(CH2—C6H4—C12H25)(O—CH2P(OH)2)—(CH2)4— Br⊖ |
| 10. | —⊕N(CH2P(OH)2=O)(C12H25)—(CH2)4— Br⊖ |

The methylene phosphonate group may be in the free acid or salt form. The salt moiety can vary widely to include any suitable metal, ammonia, amine, etc., cation such as an alkali metal, i.e., sodium, potassium, etc., a monoamine such as methyl amine, ethyl amine, etc., polyamines such as ethylene diamine, propylene diamine, the corresponding polyamines such as diethylene triamine, triethylene tetramines, etc.; alkanolamines such as ethanolamine, diethanolamine, propanolamines, etc.; cyclic-amines such as piperidine, morpholine, etc. Thus, any salt moiety capable of carrying out this invention can be employed.

Thus, the term "methylene phosphonate" includes

groups as well as substituted methylene groups, i.e.,

where R is the group derived from the aldehyde or ketone reacted, for example, those stated herein. The phosphonate can exist as the free acid or as the salt

where M is hydrogen or a salt moiety.

USE AS SCALE INHIBITOR

Scale formation from aqueous solutions containing an oxide variety of scale forming compounds, such as calcium, barium and magnesium carbonate, sulfate, silicate, oxalates, phosphates, hydroxides, fluorides and the like are inhibited by the use of threshold amounts of the compositions of this invention which are effective in small amounts, such as less than 100 ppm, and are preferably used in concentrations of less than 25 ppm.

The compounds of the present invention (e.g., the acid form of the compounds) may be readily converted into the corresponding alkali metal, ammonium or alkaline earth metal salts by replacing at least half of the hydrogen ions in the phosphonic acid group with the appropriate ions, such as the potassium ion or ammonium or with alkaline earth metal ions which may be converted into the corresponding sodium salt by the addition of sodium hydroxide. If the pH of the amine compound is adjusted to 7.0 by the addition of caustic soda, about one half of the —OH radicals on the phosphorous atoms will be converted into the sodium salt form.

The scale inhibitors of the present invention illustrate improved inhibiting effect at high temperatures when compared to prior art compounds. The compounds of the present invention will inhibit the deposition of scale-forming alkaline earth metal compounds on a surface in contact with aqueous solution of the alkaline earth metal compounds over a wide temperature range. Generally, the temperatures of the aqueous solution will be at least 40° F., although significantly lower temperatures will often be encountered. The preferred temperature range for inhibition of scale deposition is from about 130° to about 350° F. The aqueous solutions or brines requiring treatment generally contain about 50 ppm to about 50,000 ppm of scale-forming salts. The compounds of the present invention effectively inhibit scale formation when present in an amount of from 0.1 to about 100 ppm, and preferably 0.2 to 25 ppm wherein the amounts of the inhibitor are based upon the total aqueous system. There does not appear to be a concentration below which the compounds of the present invention are totally ineffective. A very small amount of the scale inhibitor is effective to a correspondingly limited degree, and the threshold effect is obtained with less than 0.1 ppm. There is no reason to believe that this is the minimum effective concentration. The scale inhibitors of the present invention are effective in both brine, such as sea water, and acid solutions.

In the specific examples the general method of phosphomethylolation is that disclosed in Netherlands Pat. Nos. 6,407,908 and 6,505,237 and in the Journal of Organic Chemistry, Vol. 31, No. 5, 1603–1607 (May, 1966). These references are hereby incorporated by reference.

Calcium Scale Inhibition Test

The procedure utilized to determine the effectiveness of the scale inhibitors in regard to calcium scale is as follows:

Several 50 ml. samples of a 0.04 sodium bicarbonate solution are placed in 100 ml. bottles. To these solutions is added the inhibitor in various known concentrations. 50 ml. samples of a 0.02 M $CaCl_2$ solution are then added.

A total hardness determination is then made on the 50—50 mixture utilizing the well known Schwarzenbach titration. The samples are placed in a water bath and heated at 180° F. 10 ml. samples are taken from each bottle at 2 and 4 hour periods. These samples are filtered through millipore filters and the total hardness of the filtrates are determined by titration.

$$\frac{\text{Total hardness after heating}}{\text{Total hardness before heating}} \times 100 = \% \text{ inhibition}$$

The tables describe the scale inhibition test results obtained for specific compositions.

The following examples illustrate the reaction of a phosphomethylated polyamine with a chain extender, i.e., dihalide.

GROUP A

Example A1

Into a suitable reaction vessel were charged 41 g. of $(H_2PO_3CH_2)_2NCH_2CH_2N(CH_2PO_3H_2)_2$ and 50 ml. of water. To the resulting solution was added 12.5 g of 1,4-dichlorobutene-2. This mixture was stirred and heated at reflux temperatures until homogeneous (24 hours). The product was a viscous liquid that was quite soluble in additional water.

Example A2

Into a suitable reaction vessel were charged 41 g. of $(H_2PO_3CH_2)_2NCH_2CH_2N(CH_2PO_3H_2)_2$ and 50 ml. of water. To the resulting solution was added 21.6 g. of 1,4-dibromobutane. The resulting mixture was stirred and heated at reflux temperatures for 24 hours. The product solution was quite viscous and water soluble.

Example A3

Into a suitable reaction vessel were charged 42.5 g. of $(H_2PO_3CH_2)_2NCH_2CH_2CH_2N(CH_2PO_3H_2)_2$ and 50 ml. of water. To the resulting solution was added 12.5 g. of 1,4-dichlorobutene-2. The resulting mixture was stirred and heated at reflux temperatures for 24 hours. The resulting product solution was viscous and soluble in additional water.

Since the examples described herein are similarly prepared, they will be presented in Table II to save repetitive details.

TABLE II $$-\underset{\underset{CH_2PO_3H_2}{|}}{\overset{\overset{CH_2PO_3H_2}{|}}{N^{\oplus}}}-R-\underset{\underset{CH_2PO_3H_2}{|}}{\overset{\overset{CH_2PO_3H_2}{|}}{N^{\oplus}}}-R'-$$

$$X^{\ominus} \quad X^{\ominus}$$

| Example | R | R' | X |
|---|---|---|---|
| A4 | (CH$_2$)$_4$ | (CH$_2$)$_4$ | Br |
| A5 | (CH$_2$)$_4$ | CH$_2$—CH=CH—CH$_2$ | Cl |
| A6 | (CH$_2$)$_4$ | (CH$_2$)$_5$ | Br |
| A7 | (CH$_2$)$_3$ | (CH$_2$)$_4$ | Br |
| A8 | (CH$_2$)$_2$ | H$_2$C—C$_6$H$_4$—CH$_2$ | Cl |
| A9 | (CH$_2$)$_2$ | (CH$_2$)$_5$ | Br |
| A10 | (CH$_2$)$_6$ | (CH$_2$)$_4$ | Br |

TABLE A

Inhibiton of scale formation from a CaCO$_3$ solution at 180° F. for four hours (200 ppm CaCO$_3$)

| Inhibitor | Salt | Conc. (ppm) | % Scale Inhibitor |
|---|---|---|---|
| Example A1 | H | 20 | 59 |
| Example A1 | H | 50 | 64 |
| Example A2 | H | 20 | 57 |
| Example A2 | H | 50 | 66 |
| Example A3 | H | 20 | 52 |
| Example A3 | H | 50 | 61 |
| Example A4 | H | 20 | 61 |
| Example A4 | H | 50 | 68 |
| Example A4 | Na | 20 | 59 |
| Example A4 | Na | 50 | 65 |
| Commercial organic phospate inhibitor | Na | 20 | 35 |
| Commercial organic phospate inhibitor | Na | 50 | 40 |
| Commercial organic phosphonate inhibitor | Na | 20 | 35 |
| Commercial organic phosphonate inhibitor | Na | 50 | 42 |

The following examples illustrate the reaction of a phosphomethylated polyamines with a non-chain extender, i.e., a monohalide.

GROUP B

Example B1

Into a small pressure reaction vessel were charged 44.0 g. of tetrakis (dihydrogen phosphonomethyl) ethylene diamine and 44 ml. of water. To this stirred solution was added 11.0 g. of methyl chloride. The resulting mixture was stirred and heated at 80° C. for 24 hours. The product solution gave a positive test with "Indiquat Test Paper" indicating the presence of quaternary ammonium salts. The product was indicated to be:

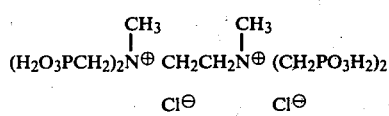

Example B2

Into a small pressure reaction vessel were charged 57.8 g. of pentakis (dihydrogen phosphonomethyl) diethylene triamine and 58 ml. of water. To this stirred solution was added 33.0 g. of ethyl bromide. The resulting mixture was stirred and heated at 80° C. for 24 hours. The product solution was completely soluble in water. The product was indicated to be:

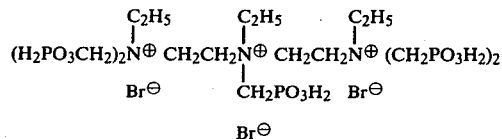

A portion of the product was neutralized with 50% NaOH.

Example B3

Into a suitable pressure reaction vessel was introduced 144 g. of a 50% aqueous solution of hexakis (dihydrogen phosphonomethyl) triethylene-tetramine. To this solution was added 21 g. of methyl chloride. This mixture was stirred and heated at 80° C. for 24 hours. The product was indicated to be:

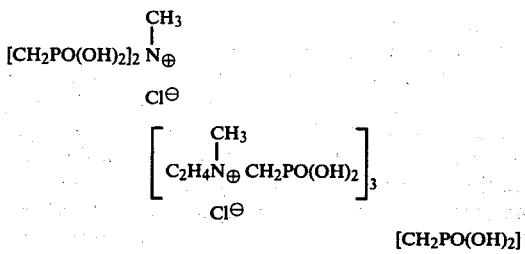

A portion of this product was converted into the ammonium salt with aqueous ammonium hydroxide.

Example B4

Into a suitable pressure reaction vessel was introduced 172 g. of a 50% aqueous solution of heptakis (dihydrogen phosphonomethyl) tetraethylene pentamine. To this solution was added 71 g. of methyl iodide. The resulting mixture was stirred and heated at 80° C. for 8 hours. The resulting solution was homogeneous and dissolved easily in water. The product was indicated to be:

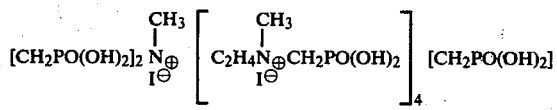

A portion of the product was neutralized with aqueous KOH.

Example B5

Into a suitable pressure reaction vessel were introduced 53 g. of tetrakis (dihydrogen phosphonomethyl) diethylene triamine N-hydroxyethyl and 53 ml. of water. To this solution was added 15.5 g. of methyl chloride. The mixture was stirred and heated at 80° C. for 24 hours. The product was indicated to be:

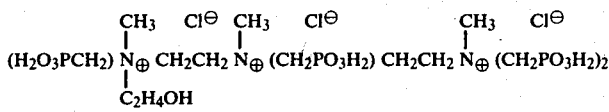

Since the examples described herein are similarly prepared, they will be presented in Table III to save repetitive details.

TABLE III

Example B6

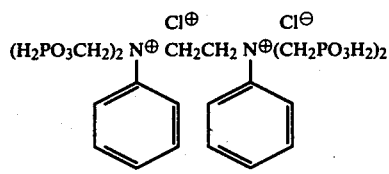

Example B7

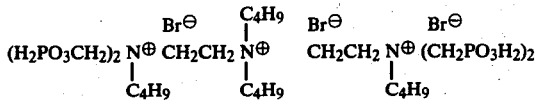

Example B8

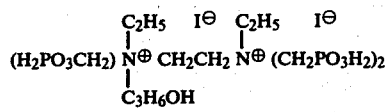

Example B9

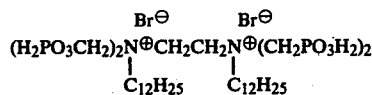

Example B10

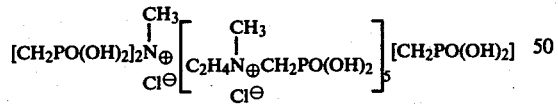

TABLE B

Inhibition of Scale Formation from a CaCO₃ solution at 180° F. four hours (200 ppm CaCO₃).

| Inhibitor | Salt | Conc. (ppm) | % Scale Inhibition |
|---|---|---|---|
| Example B1 | H | 50 | 54 |
| Example B1 | H | 20 | 50 |
| Example B2 | H | 50 | 67 |
| Example B2 | H | 20 | 57 |
| Example B2 | Na | 50 | 60 |
| Example B2 | Na | 20 | 53 |
| Example B3 | H | 50 | 52 |
| Example B3 | H | 20 | 45 |
| Example B3 | Na | 50 | 50 |
| Example B3 | Na | 20 | 40 |
| Example B4 | H | 50 | 64 |
| Example B4 | H | 20 | 50 |
| Example B5 | H | 50 | 60 |

TABLE B-continued

Inhibition of Scale Formation from a CaCO₃ solution at 180° F. four hours (200 ppm CaCO₃).

| Inhibitor | Salt | Conc. (ppm) | % Scale Inhibition |
|---|---|---|---|
| Example B5 | 20 | 45 | |
| Example B5 | Na | 50 | 55 |
| Example B5 | Na | 20 | 48 |
| Commercial Organic phosphate inhibitor | Na | 50 | 40 |
| " | Na | 20 | 35 |
| Commercial Organic phosphonate inhibitor | Na | 50 | 42 |
| " | Na | 20 | 35 |

The following examples illustrate the reaction of phosphomethylolated monoamines with difunctional dihalides.

GROUP C

Example C1

Into a suitable reaction vessel were charged 26.4 g. of $C_4H_9N(CH_2PO_3H_2)_2$ and 26.4 of water. This mixture was neutralized with 50% NaOH. To the resulting solution was added 6.3 g. of 1,4-dichlorobutene-2. This mixture was heated to reflux and held there until homogeneous (5 hours). The product was:

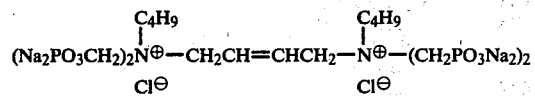

Example C2

Into a suitable reaction vessel were charged 14.5 g. of $C_6H_{11}N(CH_2PO_3H_2)_2$ and 14.5 g. of water. This mixture was neutralized with 50% NaOH. To the resulting solution was added 5.4 g. of 1,4-dibromobutane. This mixture was heated to reflux and held there until homogeneous (6 hours). The solution gave a positive test with "Indiquat Test Paper" indicating the presence of quaternary nitrogen groups.

The product was:

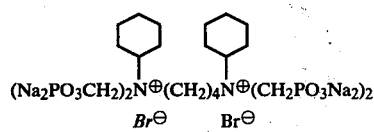

Example C3

Into a suitable reaction vessel were charged 20 g. of $C_{12}H_{25}N(CH_2PO_3H_2)_2$, 20 g. of water and 10 g. of isopropanol. This mixture was neutralized with 50% NaOH. To the resulting solution was added 5.4 g. of 1,4-dibromobutane. This mixture was heated to reflux and held there for 5 hours. The product solution dissolved easily in water and foamed strongly. The product was:

$$(Na_2PO_3CH_2)_2\overset{\underset{\displaystyle C_{12}H_{25}}{|}}{N^{\oplus}}(CH_2)_4\overset{\underset{\displaystyle C_{12}H_{25}}{|}}{N^{\oplus}}(CH_2PO_3Na_2)_2$$
$$Br^{\ominus} \quad\quad Br^{\ominus}$$

Since the examples described herein are similarly prepared, they will be presented in Table IV to save repetitive details.

TABLE IV $$(H_2PO_3CH_2\overset{\underset{\displaystyle R}{|}}{N^{\oplus}}\sim\sim\overset{\underset{\displaystyle R}{|}}{N^{\oplus}}(CH_2PO_3H_2)_2$$
$$X^{\ominus} \quad\quad X^{\ominus}$$

| Example | R | | X |
|---|---|---|---|
| C4 | $C_2H_5$ | $CH_2CH_2OCH_2CH_2$ | Cl |
| C5 | $C_3H_7$ | $CH_2CH_2$ | Br |
| C6 | $CH_3$ | $H_2C-\phenyl-CH_2$ | Cl |
| C7 | phenyl | $CH_2CH_2$ | Br |
| C8 | $C_2H_4OH$ | $CH_2CH=CHCH_2$ | Cl |
| C9 | $C_2H_5$ | $CH_2CH_2CH_2CH_2$ | Br |
| C10 | $C_{12}H_{25}$ | $CH_2CH_2$ | Br |
| C11 | $C_{14}H_{29}$ | $CH_2CH_2CH_2CH_2$ | Br |
| C12 | $C_{18}H_{37}$ | $CH_2CH_2$ | Br |

$$(H_2PO_3CH_2)\overset{\underset{\displaystyle R}{|}}{N^{\oplus}}\sim\sim\overset{\underset{\displaystyle R}{|}}{N^{\oplus}}(CH_2PO_3H_2)$$
$$R\ X^{\ominus} \quad R\ X^{\ominus}$$

| | | | |
|---|---|---|---|
| C13 | $C_2H_5$ | $CH_2CH_2CH_2CH_2$ | Br |
| C14 | tetrahydropyranyl | $CH_2CH_2$ | Br |
| C15 | $C_2H_4OH$ | $CH_2CH=CHCH_2$ | Cl |
| C16 | phenyl | $CH_2CH_2$ | Br |
| C17 | phenyl | $CH_2CH_2CH_2CH_2CH_2CH_2$ | Br |
| C18 | $C_3H_9$ | $HC_2-\phenyl-CH_2$ | Br |

TABLE C

Inhibiton of Scale Formatin from a CaCO$_3$ solution at 180° F. for four hours (200 ppm CaCO$_3$).

| Inhibitor | Salt | Conc. (ppm) | % Scale Inhibition |
|---|---|---|---|
| Example C1 | Na | 50 | 64 |
| Example C1 | Na | 20 | 54 |
| Example C2 | Na | 50 | 68 |
| Example C2 | Na | 20 | 59 |
| Example C2 | H | 50 | 70 |
| Example C2 | H | 20 | 59 |
| Example C4 | Na | 50 | 65 |
| Example C4 | Na | 20 | 55 |
| Example C13 | Na | 50 | 48 |
| Example C13 | Na | 20 | 40 |
| Example C15 | Na | 50 | 65 |
| Example C15 | Na | 20 | 59 |

USE IN THE CHELATION OR SEQUESTRATION OF METAL IONS

The chelating or sequestering agents of the present invention are of wide utility such as when it becomes necessary to sequester or inhibit the precipitation of metal cations from aqueous solutions. Among their many uses are the following applications:

Soaps and detergents, textile processing, metal cleaning and scale removal, metal finishing and plating, rubber and plastics, industry, pulp and paper industry, oil-well treatment, chelation in biological systems.

An important function of these compounds is their ability to sequester $Fe^{+2}$. In secondary oil recovery by means of water floods, waters are frequently mixed on the surface prior to injection. Frequently these waters contain amounts of $Fe^{+2}$ and $H_2S$. If these incompatible waters are mixed, an FeS precipitate results which can plug the sand face of the injection well. Another of their functions is to prevent formation of gelatinous iron hydroxides in the well and in the effluent production waters.

To demonstrate the effectiveness of the polyquaternary ammonium methylene phosphonates in chelating $Fe^{+2}$, the following test procedure was utilized. Into a flask that contained a known concentration of the sequestering agent, and enough sodium hydroxide or hydrochloric acid to give the desired pH was placed a 100 ml. aqueous sample of ferrous ammonium sulfate (20 ppm of $Fe^{+2}$); after final pH adjustment the solution was allowed to remain at ambient temperatures for 48 hours. The solution was centrifuged for one hour to remove collodial iron hydroxide and an aliquot of the supernatant solution was analyzed by atomic absorption to determine the iron concentration.

The following table illustrates the ability of the sequestering agents of the present invention to sequester $Fe^{+2}$, as compared to the well known sequestering agent tetrasodium ethylenediamine tetra-acetate (EDTA).

TABLE V

| pH | Sequestering Agent (ppm) | Amount of iron Sequestered (ppm) |
|---|---|---|
| 5 | A1 (50) | (12) |
| 5 | A2 (50) | (9) |
| 5 | B1 (50) | (7) |
| 5 | C1 (50) | (14) |
| 5 | EDTA (50) | (7) |
| 7 | A1 (50) | (12) |
| 7 | A2 (50) | (9) |
| 7 | B1 (50) | (7) |
| 7 | C1 (50) | (13) |
| 7 | EDTA (50) | (7) |
| 10 | A1 (150) | (9) |
| 10 | A2 (150) | (7) |
| 10 | B1 (150) | (6) |
| 10 | C1 (150) | (10) |
| 10 | EDTA (150) | (6) |

As one can observe from the preceding table, the sequestering agents of this invention are as effective, and in some cases superior, to EDTA when tested over a wide pH range.

The sequestering agents of this invention are also quite effective in sequestering other metal cations in aqueous solutions. For example, a test was conducted in which 60 ppm of the sequesterant were dissolved in 100 ml. of water. The pH was adjusted to 9 and maintained there. Metal cations were added, in the following amounts, before a noticeable precipitate was formed.

TABLE VI

| Sequesterant | Metal (ppm) Sequestered per 60 ppm of Sequesterant | |
|---|---|---|
| Product | | |
| Example A1 | $Fe^{+3}$ | (70) |
| Example A1 | $Al^{+3}$ | (120) |
| Example A1 | $Cu^{+2}$ | (120) |

TABLE VI-continued

| Sequesterant | Metal (ppm) Sequestered per 60 ppm of Sequesterant | |
|---|---|---|
| Example A1 | $Ni^{+2}$ | (60) |
| Example B1 | $Fe^{+3}$ | (60) |
| Example B1 | $Al^{+3}$ | (70) |
| Example B1 | $Cu^{+2}$ | (70) |
| Example B1 | $Ni^{+3}$ | (50) |

Other heavy metals sequestered by the sequestering agents of this invention such as cobalt, manganese, chromium and the like.

The amount employed to chelate is controlled by stoichiometry in contrast to scale inhibition where the amount employed is threshold or less than stoichiometric.

USE AS A MICROBIOCIDE

I. In Water Treatment

This phase of the present invention relates to the treatment of water. More particularly, it is directed to providing improved means for controlling microbiological organisms including bacteria, fungi, algae, protozoa, and the like, present in water.

It is well known that ordinary water contains various bacteria, fungi, algae, protozoa and other microbiological organisms which, if uncontrolled, multiply under certain conditions so as to present many serious problems. For example, in swimming pools the growth of these microbiological organisms is very undesirable from a sanitary standpoint as well as for general appearances and maintenance. In industrial water systems such as cooling towers, condenser boxes, spray condensers, water tanks, basins, gravel water filters, and the like, microbiological organisms may interfere greatly with proper functioning of equipment and result in poor heat transfer, clogging of systems and rotting of wooden equipment, as well as many other costly and deleterious effects.

In other industrial applications where water is used in processes, as for example, as a carrying medium, etc., microbiological organisms may also constitute a problem in maintenance and operation. Illustrative of such industrial applications are the pulp and paper manufacturing processes, oil well flooding operations and the like.

The products of this invention are suitable as biocides for industrial, agricultural and horticultural, military, hygienic and recreational water supplies. They provide an inexpensive, easily prepared group of products which can be used, in minimal amounts, in water supplies, in cooling towers, air-conditioning systems, on the farm and ranch, in the factory, in civilian and military hospitals and dispensaries, in camps, for swimming pools, baths and aquaria, waterworks, wells, reservoirs, by fire-fighting agencies, on maritime and naval vessels, in boilers, steam-generators and locomotives, in pulp and paper mills, for irrigation and drainage, for sewage and waste disposal, in the textile industry, in the chemical industries, in the tanning industry, et cetera, and which will render said water supplies bactericidal, fungicidal and algicidal. They further provide a simple process whereby water supplies, for whatever purposes intended, are rendered bacteriostatic, fungistatic and algistatic, i.e., said water supplies treated by the process of this invention will resist and inhibit the further growth or proliferation of bacteria, fungi, algae and all forms of microbial life therein.

II. Water Flooding in Secondary Recovery of Oil

This phase of the present invention relates to secondary recovery of oil by water flooding operations and is more particularly concerned with an improved process for treating flood water and oil recovery therewith. More particularly this invention relates to a process of inhibiting bacterial growth in the recovery of oil from oil-bearing strata by means of water flooding taking place in the presence of sulfate-reducing bacteria.

Water flooding is widely used in the petroleum industry to effect secondary recovery of oil. By employing this process the yield of oil from a given field may be increased beyond the 20-30 percent of the oil in a producing formation that is usually recovered in the primary process. In flooding operations, water is forced under pressure through injection wells into or under oil-bearing formations to displace the oil therefrom to adjacent producing wells. The oil-water mixture is usually pumped from the producing wells into a receiving tank where the water, separated from the oil, is siphoned off, and the oil then transferred to storage tanks. It is desirable in carrying out this process to maintain a high rate of water injection with a minimum expenditure of energy. Any impediment to the free entry of water into oil bearing formations seriously reduces the efficiency of the recovery operation.

The term "flood water" as herein employed is any water injected into oil bearing formations for the secondary recovery of oil. In conventional operations, the water employed varies from relatively pure spring water to brine and is inclusive of water reclaimed from secondary recovery operations and processed for recycling. The problems arising from the water employed depend in part on the water used. However, particularly troublesome and common to all types of water are problems directly or indirectly concerned with the presence of microorganisms, such as bacteria, fungi and algae. Microorganisms may impede the free entry of water into oil-bearing formations by producing ions susceptible of forming precipitates, forming slime and/or existing in sufficiently high numbers to constitute an appreciable mass, thereby plugging the pores of the oil-bearing formation. Pore-plugging increases the pressure necessary to drive a given volume of water into an oil-bearing formation and oftentimes causes the flooding water to by-pass the formation to be flooded. In addition, microorganisms may bring about corrosion by acting on the metal structures of the wells involved, producing corrosive substances such as hydrogen sulfide, or producing conditions favorable to destructive corrosion such as decreasing the pH or producing oxygen. The products formed as the result of corrosive action may also be pore-plugging precipitates. Usually, the difficulties encountered are a combination of effects resulting from the activity of different microorganisms.

III. Hydrocarbon Treatment

This phase of the present invention relates to the use of these compounds as biocides in hydrocarbon systems.

In addition to being used as biocides in aqueous systems, the compounds of this invention can also be employed as biocides in hydrocarbon systems, particularly when petroleum products are stored. It is believed that bacteria and other organisms, which are introduced into hydrocarbon systems by water, feed readily on hydrocarbons resulting in a loss in product; that microorganisms cause the formation of gums, H₂S, peroxides, acids and slimes at the interface between water and oil; that bacterial action is often more pronounced with rolling motion than under static conditions, etc. Loss of product, corrosion of the storage tank, clogging of filters and metering instruments, and fuel deterioration are among the harmful effects of bacteria growth in fuels. The activity of microorganism growth is often increased by the presence of rust. Not only do these microorganisms often encourage rust but rust encourages microorganism growth. Since microorganism growth appears to be considerably higher with kerosene than with gasoline, plugged filters experienced with jet fuels which contain large amounts of kerosene is a serious problem.

The compositions of this invention can be employed in hydrocarbon systems.

Microbiocidal Testing:

The screening procedure was as follows: a one percent by weight solution of the test compound in water was prepared. The solution was aseptically added to a sterile broth that would support the growth of the test organism, Desulfovibro desulfuricans, to provide a concentration of 50 and 100 parts by weight of test compound per million parts by weight of broth. A general growth medium, such as prescribed by the American Petroleum Institute was used. The broth containing the test compound then was dispersed in 5 cc. amounts into sterile disposable tubes and the tubes were inoculated with the growing test organism and incubated at 35° C. for 24 hours. The absence or presence of growth of the microorganisms was determined by visual inspection by an experienced observer.

Following is a summary of the results of the testing of examples of this invention.

| Compound Example # | Concentration of Test Compound | Results |
| --- | --- | --- |
| C3 | 25 ppm | *Gave control |
| C10 | 25 ppm | Gave control |
| C11 | 40 ppm | Gave control |

*by control is meant that the test compound was biostatic or biocidal -- i.e., no growth of the test organism occurred under the test conditions.

I claim:

1. The process of controlling microbiological growth in an aqueous system which comprises adding to said system a microbiologically effective amount of a polyquaternary compound having the repeating unit of the formula

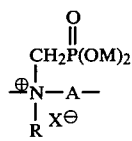

where R is

alkyl, aryl, alkenyl, alkaryl, aralkyl or cycloalkyl, A is alkylene having 2 to 10 carbon atoms, alkaralkylene having 8 to 20 carbon atoms, dialkylene ether wherein each alkylene group has 1 to 10 carbon atoms, alkenylene, or alkinylene; M is hydrogen, ammonium, an alkali metal or alkaline earth metal; X is Br, I or Cl.

2. The process of controlling microbiological growth in an aqueous system which comprises adding to said system a microbiologically effective amount of a polyquaternary compound where the polyquaternary compound has the repeating unit of the formula

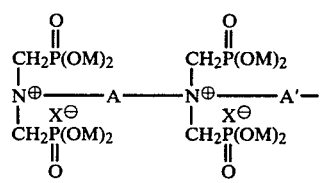

A is alkylene having 2 to 10 carbon atoms; A' is alkylene having 2 to 25 carbon atoms, alkaralkylene having 8 to 20 carbon atoms, dialkylene ether wherein each alkylene group has 1 to 10 carbon atoms, alkenylene and alkinylene; M is hydrogen, ammonium, an alkali metal or alkaline earth metal; X is Br, I or Cl.

3. The process of controlling microbiological growth in an aqueous system which comprises adding to said system a microbiologically effective amount of a polyquaternary compound where the polyquaternary compound has the formula

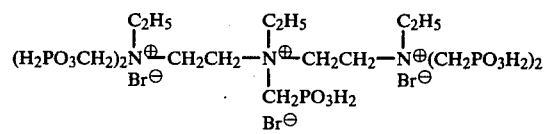

4. The process of controlling microbiological growth in an aqueous system which comprises adding to said system a microbiologically effective amount of a polyquaternary compound where the polyquaternary compound has the formula

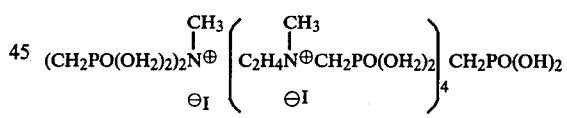

5. The process of claim 1 where the aqueous system is a water flooding system in the secondary recovery of oil.

6. The process of claim 1 where the aqueous system is an industrial water system.

7. The process of claim 2 where the aqueous system is a water flooding system in the secondary recovery of oil.

8. The process of claim 2 where the aqueous system is an industrial water system.

9. The process of claim 3 where the aqueous system is a water flooding system in the secondary recovery of oil.

10. The process of claim 4 where the aqueous system is a water flooding system in the secondary recovery of oil.

* * * * *